(12) United States Patent
Wagner

(10) Patent No.: US 7,762,971 B2
(45) Date of Patent: Jul. 27, 2010

(54) TILT-STABLE ROTATING JOINT AND TECHNICAL ORTHOPEDIC COMPONENT CONSTRUCTED THEREWITH

(75) Inventor: Helmut Wagner, Duderstadt (DE)

(73) Assignee: Otto Bock HealthCare GmbH, Duderstadt (DE)

(*) Notice: Subject to any disclaimer, the term of this patent is extended or adjusted under 35 U.S.C. 154(b) by 249 days.

(21) Appl. No.: 11/718,889

(22) PCT Filed: Nov. 8, 2005

(86) PCT No.: PCT/DE2005/002025

§ 371 (c)(1),
(2), (4) Date: May 8, 2007

(87) PCT Pub. No.: WO2006/048012

PCT Pub. Date: May 11, 2006

(65) Prior Publication Data

US 2007/0276503 A1    Nov. 29, 2007

(30) Foreign Application Priority Data

Nov. 8, 2004    (DE) .................. 10 2004 054 384

(51) Int. Cl.
*A61F 5/00* (2006.01)
(52) U.S. Cl. .............................. 602/16; 602/20; 602/23
(58) Field of Classification Search ............... 602/5, 602/16, 20–23, 26–27; 128/882
See application file for complete search history.

(56) References Cited

U.S. PATENT DOCUMENTS 5,370,701 A * 12/1994 Finn .................. 623/20.25

FOREIGN PATENT DOCUMENTS

| DE | 269084 | 5/1911 |
| EP | 0 704 194 A1 | 4/1996 |
| GB | 228 284 A | 2/1925 |

OTHER PUBLICATIONS

International Search Report for PCT/DE2005/002025.

* cited by examiner

*Primary Examiner*—Michael A. Brown
(74) *Attorney, Agent, or Firm*—Faegre & Benson, LLP

(57) ABSTRACT

The invention relates to a tilt-stable rotating joint suitable for technical orthopedic components, including a forked external joint part with two limbs whose parallel inner walls pointing towards each other form a slit of a given width and are provided with flush continuous holes. A flat inner joint part protrudes into the slit and a continuous hole, and a shaft arrangement protruding through the continuous holes forms a rotating bearing surface with a cover surface. The tilt-stability is increased because the shaft arrangement is formed by sections protruding from the inner joint part, having an external diameter corresponding to the internal diameter of the continuous holes of the limbs. Stability is also increased by the fact that the shaft arrangement is rotationally fixed to the inner joint part and sliding bearings are formed between the walls of the continuous holes of the limbs and the sections of the shaft arrangement.

19 Claims, 7 Drawing Sheets

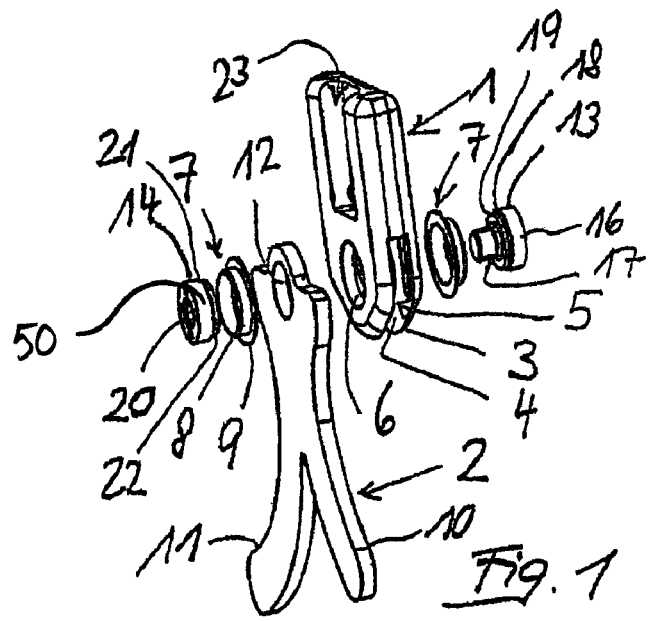
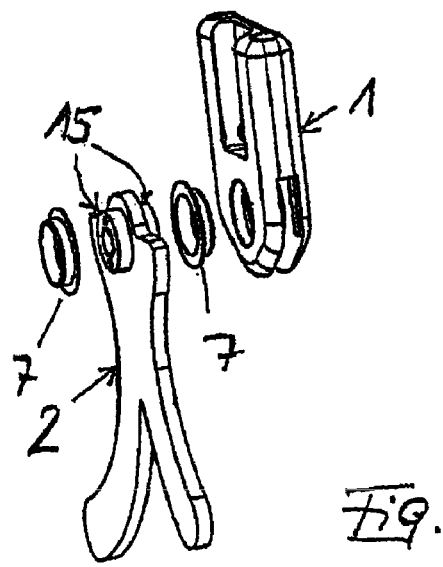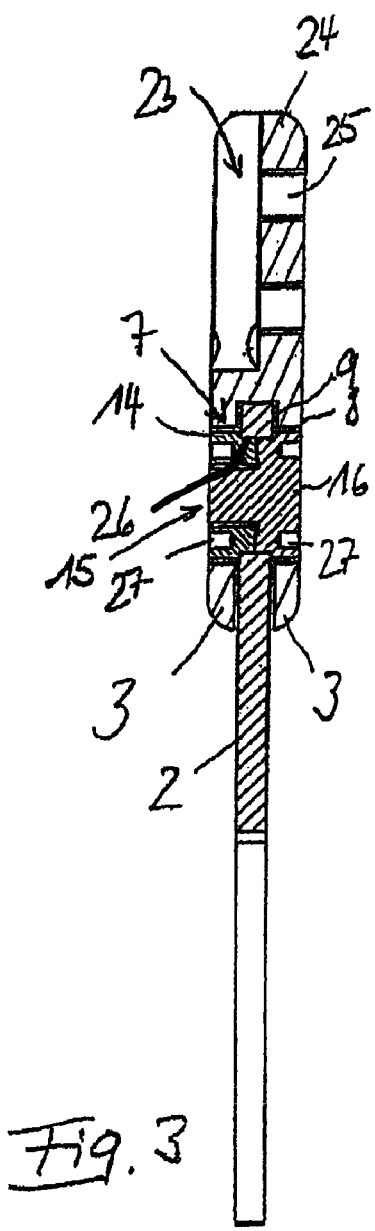
Fig. 1
Fig. 2
Fig. 3

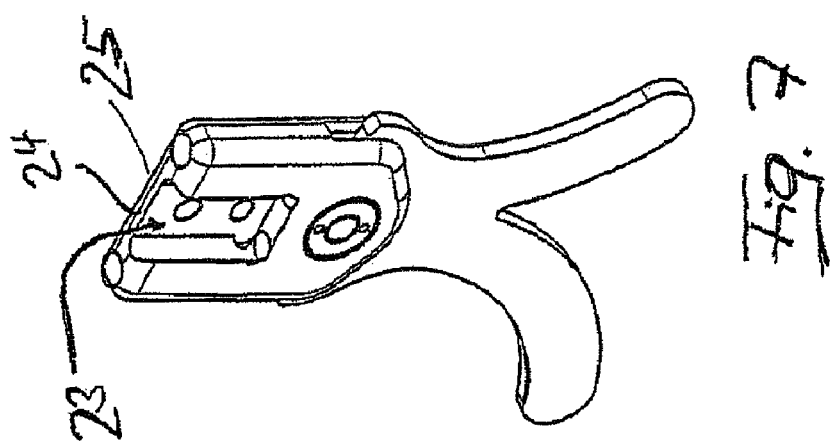
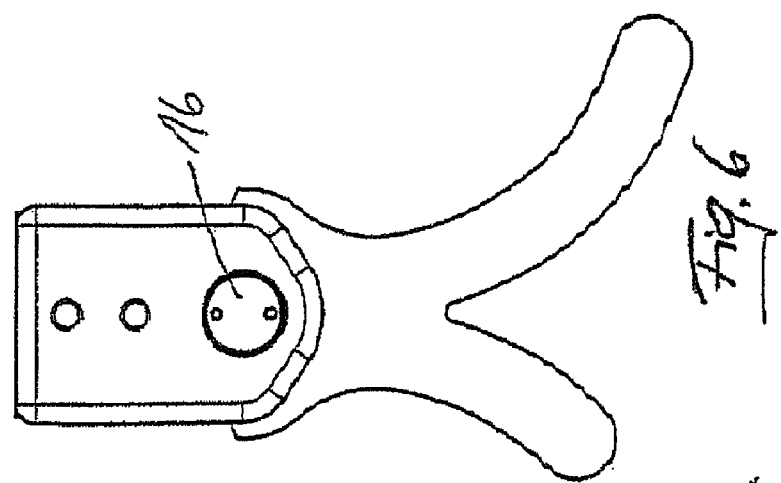
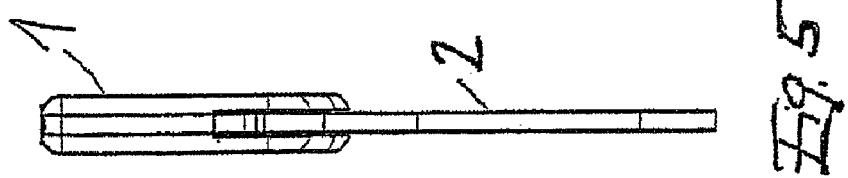
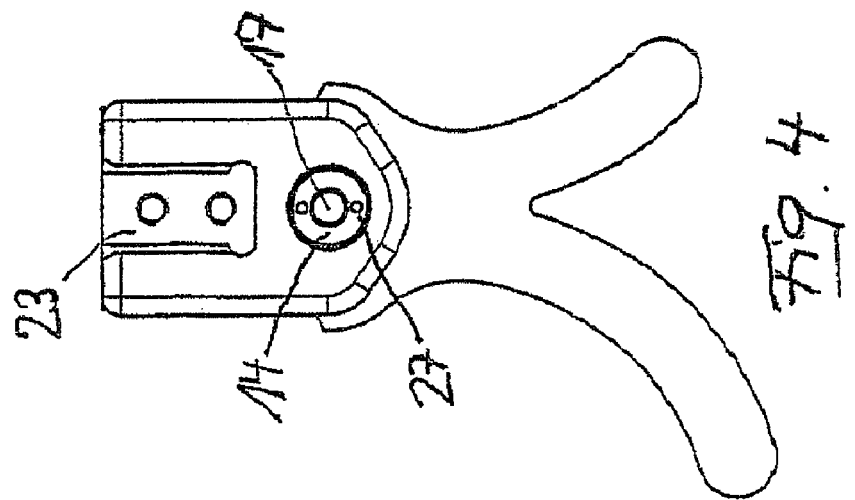

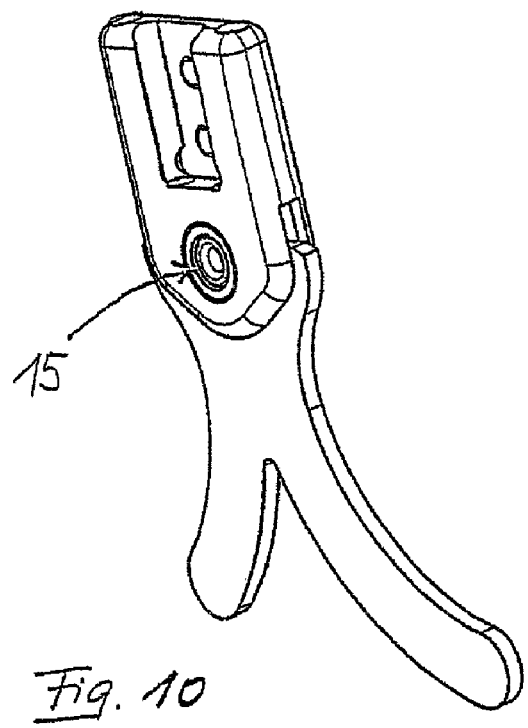
Fig. 10
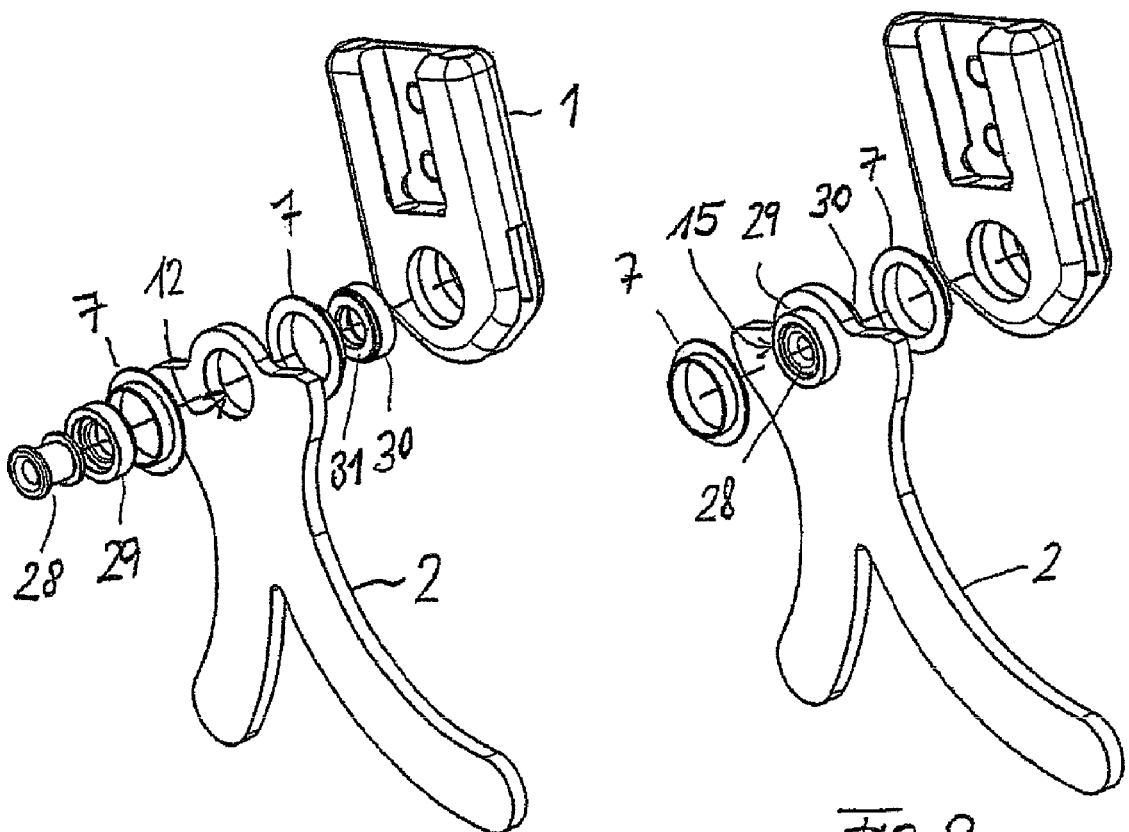
Fig. 8
Fig. 9

TILT-STABLE ROTATING JOINT AND TECHNICAL ORTHOPEDIC COMPONENT CONSTRUCTED THEREWITH

This patent application is the national stage of International Application No. PCT/DE2005/002025, which claims priority to German Application No. 10 2004 054 384.4 filed on Nov. 8, 2004; the entire contents of both applications are hereby expressly incorporated by reference.

TECHNICAL FIELD

The invention relates to a tilt-stable rotating joint for an orthopedic component.

BACKGROUND OF THE INVENTION

Tilt-stable rotating joints are needed in a wide variety of applications. The design of a tilt-stable rotating joint is particularly problematic if only a limited space is available for the rotating joint and if, consequently, the rotating joint has to be made especially flat in order not to appear too bulky.

Rotating joints of this kind are needed in particular in technical orthopedic components, that is to say in orthoses or prostheses. Since the rotating joints have to satisfy stringent safety requirements, they need to have a high level of stability against tilting and should have no appreciable play outside their rotation plane.

Tilt-stable rotating joints of this kind, as are used in particular for orthoses, comprise a flat inner joint piece into whose through-hole a ring made of a sliding metal is pressed. The shaft arrangement is designed in the form of a screwed union, such that the screw sleeve with its smooth cylindrical jacket surface corresponds to the diameter of the ring of sliding metal that is pressed in. Both parts of the screwed union are provided with radially protruding heads that are located, preferably recessed, on the outer face of the branches. To ensure that the screwed union is connected in a rotationally fixed manner to the branches of the fork-shaped outer joint piece, one of the heads and its associated recess in the branch can be made rotationally asymmetrical, with the result that this head is mounted secure against rotation in its recess, and the screwed union therefore only has to be tightened on the other side.

SUMMARY OF THE INVENTION

The rotary bearing surface of a conventional rotating joint of the type mentioned above is formed by the through-opening in the inner joint piece, such that the tilt stability has to be generated only via an annular bearing surface arising from the material thickness of the inner joint piece. The tilt stability of the rotating joint is obtained from precise manufacture with low production tolerances between the cylindrical jacket surface of the screwed union and the pressed-in ring made of a sliding metal.

The object of the present invention is to improve the tilt stability of the rotating joint of the type mentioned at the outset.

To achieve this object, a tilt-stable rotating joint of the type mentioned at the outset is characterized in that the shaft arrangement is formed by sections which protrude from the inner joint piece and have an external diameter corresponding to the internal diameter of the through-holes of the branches. In addition, the shaft arrangement is connected in a rotationally fixed manner to the inner joint piece, and slide bearings are formed between the walls of the through-holes of the branches and the sections of the shaft arrangement.

The rotary bearing surface of a conventional rotating joint of the type mentioned at the outset is formed by the through-opening in the inner joint piece, such that the tilt stability has to be generated only via an annular bearing surface arising from the material thickness of the inner joint piece. The rotating joint according to the invention comprises includes a rotationally fixed unit between the inner joint piece and the shaft arrangement, such that the joint is supported between the shaft arrangement and the walls of the though-holes of the branches. The support is thus achieved on both cylindrical jacket surfaces of the shaft arrangement in the area of the branches, such that the shaft arrangement is supported according to the invention on two slide bearings spaced apart from one another. This ensures a considerable enlargement of the slide-bearing surface and improved tilt stability.

In one embodiment of the invention, annular edges of the through-holes between the inner walls of the branches and the surfaces of the inner joint piece are also designed as slide bearings. The edges of the inner walls are preferably designed as slide bearings and protrude as raised edges from the rest of the respective inner wall, such that a defined annular bearing surface between inner wall and inner joint piece is obtained at the edge of the through-opening.

The wall of the through-holes of the branches is preferably formed by in each case an inserted slide-bearing sleeve. As an alternative to this, it is possible also to provide the surface of the screwed union in the sections of greatest external diameter with a slide coating.

In one embodiment of the slide-bearing sleeves inserted into the through-holes, these are, in each case, provided with a circular flange that bears on the inner walls of the branches. The inserted sleeves thus form both the radial slide bearings in the walls of the through-holes and also the axial annular slide bearings on the inner walls of the branches The material thickness of the slide-bearing sleeves is preferably less than about 0.039 inches (about 1 mm) and is preferably between about 0.016 and about 0.028 inches (about 0.4 and about 0.7 mm), preferably about 0.020 inches (about 0.5 mm).

The slide-bearing sleeves can be pressed into the through-holes of the branches. Other connection techniques, such as adhesive bonding or welding, are also possible. It is also possible to design the surfaces in question as slide bearings by means of a chemical or physical surface modification.

In one embodiment of the invention, the shaft arrangement is formed by a screwed union composed of a screw and a screw bushing. The sections protruding from the inner joint pieces can have a greater external diameter, such that the screwed union forms a radially open groove whose diameter at the groove base corresponds to the internal diameter of the through-hole of the inner joint piece. By firmly tightening the screwed union, the rotationally fixed connection between the screwed union and the inner joint piece is obtained The groove of the screwed union is preferably formed by a shoulder in the diameter of both parts of the screwed union. However, it is also conceivable to design only one part of the screwed union with a shoulder and thus form the groove with a groove base in only one part of the screwed union.

The depth of the radially open groove can be kept very small and is, for example, about 0.39 inches (about 1 mm) or less. The shoulder thus formed is entirely sufficient for creating the connection of the screwed union to the inner joint piece to form an in practice one-piece joint component.

Alternatively to being designed as a screwed union, the shaft arrangement can also be designed with a rivet arrangement which, together with bushings, forms the sections for the rotary bearing surface.

Alternatively, it is possible to press a bolt into the through-hole of the inner joint piece, the ends of the bolt protruding from the inner joint piece representing the sections for the rotary bearing surface.

Of course, it is possible to achieve the rotationally fixed connection between the shaft arrangement and the inner joint piece in many different ways. All connection techniques are conceivable, such as interlacing, welding, wedging, interference fit, etc. Also, an asymmetrical design of the through-hole and of a bolt, protruding via the through-hole, of the shaft arrangement can also be used. In addition to the inner joint piece the bolt naturally also comprises the circular cylindrical sections whose jacket surface is used to form the slide-bearing surface with the branches of the outer joint piece.

It is of course possible to dispense with the above-mentioned use of slide-bearing sleeves if a suitable sliding material is used for the shaft arrangement and the cylindrical inner wall of the through-holes in the branches of the outer joint piece. This can be done through a suitable choice of material and/or through hardening and coating the corresponding surfaces.

The fork-shaped outer joint piece does not have to be in one part and instead can be composed of two parts, which can also be held together by the shaft arrangement. Such an arrangement is useful when two inner joint pieces are designed with a toothed contour and mesh with one another. The inner joint pieces are both held in an outer joint piece composed of two cover-like parts which are arranged on both sides of the inner joint piece and form the branches of the fork-shaped outer joint piece.

BRIEF DESCRIPTION OF THE DRAWINGS

For production engineering reasons, the rotary bearing surfaces of the shaft arrangement, which form the rotary bearing together with corresponding through-holes in the branches of the outer joint piece, are preferably cylindrical. With conical rotary bearing surfaces and through-holes, for example, still greater tilt stability could be achieved, albeit with greater complexity of production.

The invention will be explained in more detail below on the basis of illustrative embodiments depicted in the drawing, in which:

FIG. 1 shows an exploded perspective view of the parts of a first embodiment of a rotating joint according to the invention, FIG. 2 shows an exploded view according to FIG. 1 with an assembled inner joint piece, FIG. 3 shows a cross section through the assembled rotating joint, FIG. 4 shows a side view of the assembled rotating joint, FIG. 5 shows a front view of the assembled rotating joint, FIG. 6 shows another side view of the assembled rotating joint, FIG. 7 shows a perspective view of the assembled rotating joint, FIG. 8 shows an exploded perspective view of parts of a second embodiment of a rotating joint according to the invention, FIG. 9 shows a perspective view illustrating the unit formed by the inner joint piece and the shaft arrangement, FIG. 10 shows a perspective view of the assembled rotating joint according to the second embodiment.

DETAILED DESCRIPTION

Figure 13:
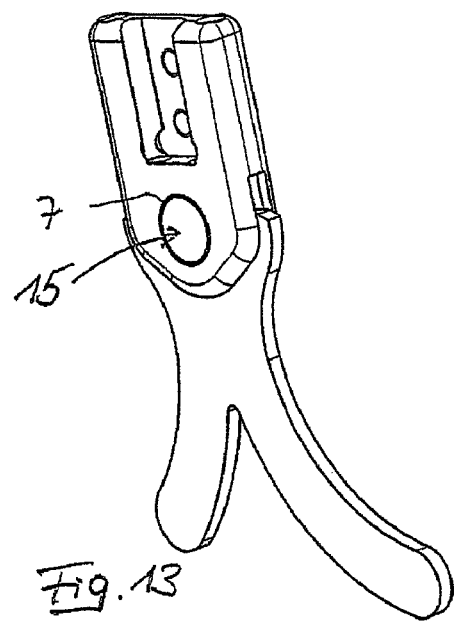
FIG. 13 shows a perspective view of the assembled rotating joint according to the third embodiment.

The first illustrative embodiment of a rotating joint according to the invention, shown in FIGS. 1 to 7, has an outer joint piece 1 and an inner joint piece 2. The outer joint piece 1 is fork-shaped at one end and has two branches 3 with parallel inner walls 4 that face each other and form a slit 5 of a predetermined constant width. In the area of the slit 5, the branches 3 are provided with circular through-holes 6 that are the same size on both branches 3 and are aligned with one another. A slide-bearing sleeve 7 can be inserted into the through-holes 6, in each case from the slit direction, that is, from inside the slit 5 outward, and extends with a cylindrical bushing part 8 across the width of the branch 3, that is to say across the entire length of the through-hole 6. The slide-bearing sleeve 7 also has a circular flange 9 that thus bears on the inner wall 4 of the associated branch 3.

The inner joint piece 2 is formed by a flat rail piece, which can have a shape suited for the particular application. In the illustrative embodiment shown, the inner joint piece 2 is designed as a lower ankle-joint piece with two arms 10, 11 bent off in opposite directions. The inner joint piece 2 can have any desired shape, for example, the shape of a rectangular holding rail. The inner joint piece 2 is made of a flat material whose material thickness at one end is such that the inner joint piece 2 can be fitted with this end into the slit 5 of the outer joint piece 1. At this end, the inner joint piece 2 has a through-hole 12 which, in the illustrative embodiment shown, has a circular shape and has a radius that is about 0.039 inches (about 1 mm) smaller than the through-holes 6 of the branches 3 of the outer joint piece 1.

The through-hole 12 is accessible via the through-holes 6 and is fixed relative to the outer joint piece 1 by a shaft arrangement 15. This is a screwed union made up of a screw 13 and of a screw bushing 14.

The screw 13 is composed of a cylindrical screw head 16 that is provided integrally with a threaded pin 17. The external diameter of the cylindrical screw head 16, is substantially similar to the internal diameter of the cylindrical bushing part 8 of the slide-bearing sleeve 7, such that the slide-bearing sleeve 7 forms a rotary bearing surface with the screw head 16. The screw head 16 also has a small shoulder 18, which is formed by a reduction in diameter and as a result of which the screw head 16 has a section 19 whose external diameter corresponds to the internal diameter of the through-hole 12 of the inner joint piece 2.

Similarly, the screw bushing 14 includes a through-opening 20, with an inner thread for receiving the threaded pin 17, and an outer cylindrical jacket surface 50 whose external diameter is substantially similar to the internal diameter of the slide-bearing sleeve 7. The width of the cylindrical jacket surface 50 is substantially similar to the width of the cylindrical bushing part 8 of the slide-bearing sleeve 7. Adjoining it, the cylindrical jacket surface 50 is provided with a shoulder 21, which is formed by a cylindrical section 22 with a slightly reduced diameter. The external diameter of the cylindrical section 22 is substantially similar to the internal diameter of the through-hole 12.

FIG. 2 illustrates that the screwed union shaft arrangement 15 forms a functionally uniform part with the inner joint piece 2. However, this can only be put together upon assembly of the rotating joint and cannot be preassembled in the manner shown in FIG. 2.

At its end remote from the through-holes 6, the outer joint piece 1 is provided with a rectangular recess 23 forming a chamber that is open toward the wide side and toward the end face and into which the end-piece of a rectangular flat rail can be inserted. The recess is delimited by a rear wall 24, in which there are two through-holes 25 for screwed fastening of the flat rail inserted into the recess 23.

FIG. 3 shows a vertical section through the rotating joint assembled from the parts shown in FIG. 1. It will be seen that the inner joint piece 2 is held in a groove 26 of the screwed union 15. This groove 26 is formed by the shoulders 18, 21 and by the adjoining sections 19, 22 of the screw head 16 and of the screw bushing 14.

At their axial end faces, the screw head 16 and the screw bushing 14 each have two diametrically opposite blind holes 27 that allow the screw 13 and the screw bushing 14 to be rotated by means of a suitable tool.

The inner joint piece 2 is mounted radially with an exact fit in the groove 26 of the screwed union 15 and bears axially on the flange 9 of the slide-bearing sleeve 7. The screwed union 15 for its part, lies with the cylindrical outer faces of screw head 16 and screw bushing 14 on the cylindrical bushing parts 8 of the slide-bearing sleeve 7. As a result, the actual rotary bearing is formed for the rotation movement of the inner joint piece 2 relative to the outer joint piece 1. During the rotation movement, a relative movement of the inner joint piece 2 with respect to the screwed union 15 will not generally take place. The connection between inner joint piece 2 and screwed union 15 can be rotationally fixed by a form-fit engagement, which can be formed, for example, by a square hole in the inner joint piece 2 and a corresponding design of the shoulders 19, 21 of the screwed union 15. In this case, the screwed union 15 has to be supplemented by an additional screw.

Whereas in conventional rotary bearings of this kind the rotary bearing is formed on the inner wall of the through-hole 12 of the inner joint piece 2 relative to a cylindrical screwed union and can therefore be supported against tilting movements only via the material thickness of the inner joint piece 2, In the first embodiment of the rotating joint according to the invention shown here, the support for the rotation movement takes place on the two bushing parts 8 of the slide-bearing sleeve 7 and thus extends along the length of the screwed union 15 and the total thickness of the outer joint piece 1 with the two branches 3, thus ensuring considerably increased stability against tilting FIG. 4 shows a side view of the assembled rotating joint from the side on which the recess 23 and the screw bushing 14 are located. The free end of the threaded pin 17 can be seen in the screw bushing 14.

FIG. 5 shows a front view of the assembled rotating joint. It can be seen that the rotating joint can be formed with a very narrow structure which, when used as an orthotic joint for example, does not look bulky on supported limbs of a human body.

FIG. 6 shows a side view of that side of the assembled rotating joint on which the screw head 16 is located.

FIG. 7 illustrates the assembled rotating joint according to the first embodiment in a perspective view.

FIGS. 8 to 10 show a second embodiment of a rotating joint according to the invention. This differs from the first embodiment only in terms of another design of the shaft arrangement 15. In this embodiment, it is formed by a rivet 28 and two bushings 29, 30, which protrude with shoulders 31 of slightly reduced external diameter into the through-hole 12 of the inner joint piece 2. As a result, they form sections with a greater external diameter which, together with the slide-bearing sleeves 7, form the slide bearing between the outer joint piece 1 and the inner joint piece 2.

FIG. 9 shows that the two bushings 29, 30 are held together by the rivet 28 and are pressed against the material of the inner joint piece 2, such that a rotationally fixed connection exists between the bushings 29, 30 and the inner joint piece 2. The view in FIG. 9 is unrealistic and for illustrative purposes only, because the bushings can be secured on the inner joint piece 2 by means of the rivet 28 only when the inner joint piece 2 has been inserted with an exact fit into the outer joint piece 1. Therefore, the view in FIG. 9 serves only to explain how the bushings 29, 30 are secured on the inner joint piece 2 in the assembled state, as is shown in FIG. 10

Figure 11:
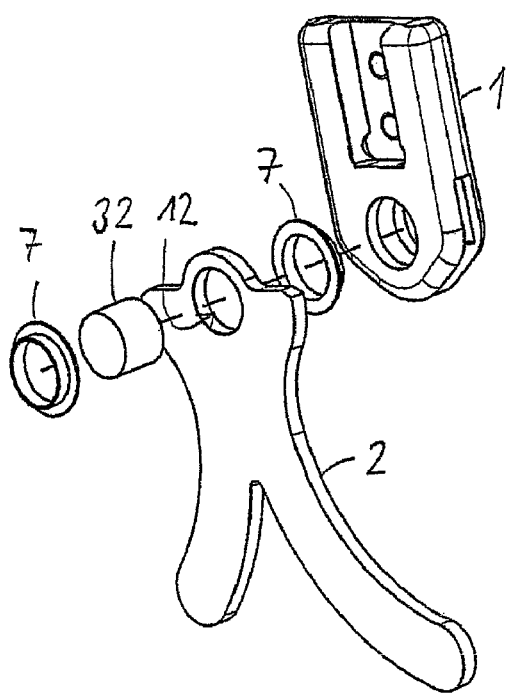
FIG. 11 shows an exploded perspective view of parts of a third embodiment of a rotating joint according to the invention.
Figure 12:
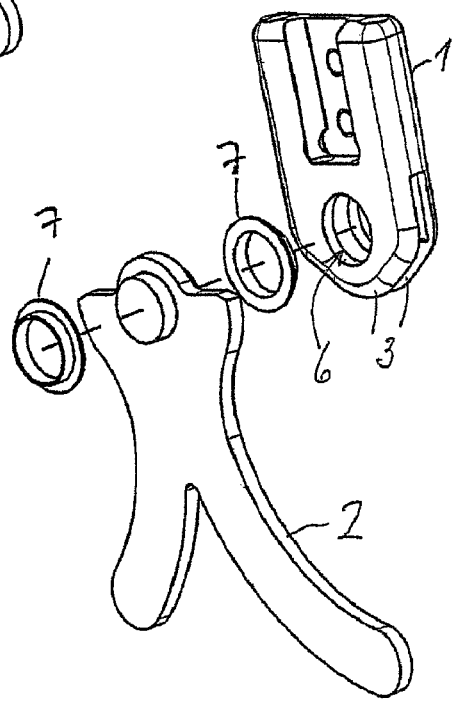
FIG. 12 shows a perspective view illustrating the unit formed by the shaft arrangement and the inner joint piece.

In the third embodiment of a rotating joint according to the invention, shown in FIGS. 11 to 13, the shaft arrangement 15 is formed by a bolt 32 which is dimensioned such that it is held in the through-opening 12 of the inner joint piece 2 by an interference fit. As is illustrated in FIG. 12, sections of the bolt 32 protrude from both sides of the inner joint piece 2 and, together with the slide-bearing sleeves 7 fitted into the through-holes 6 in the branches 3 of the outer joint piece 1, form the slide bearing shown in the assembled state in FIG. 13.

Figure 16:
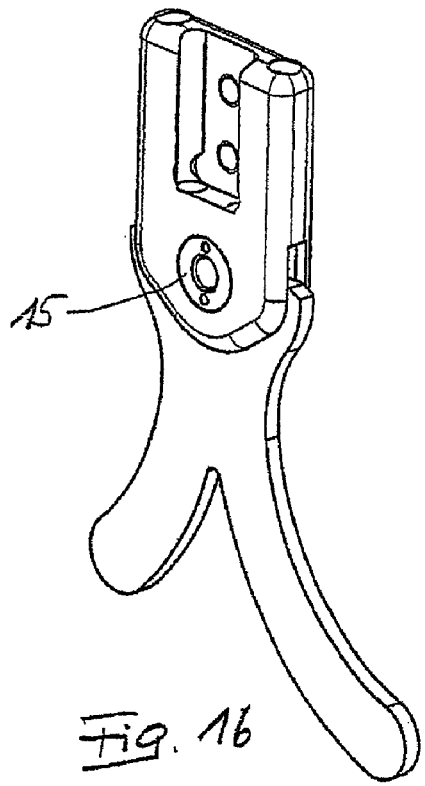
FIG. 16 shows a perspective view of the assembled rotating joint according to the fourth embodiment.
Figure 14:
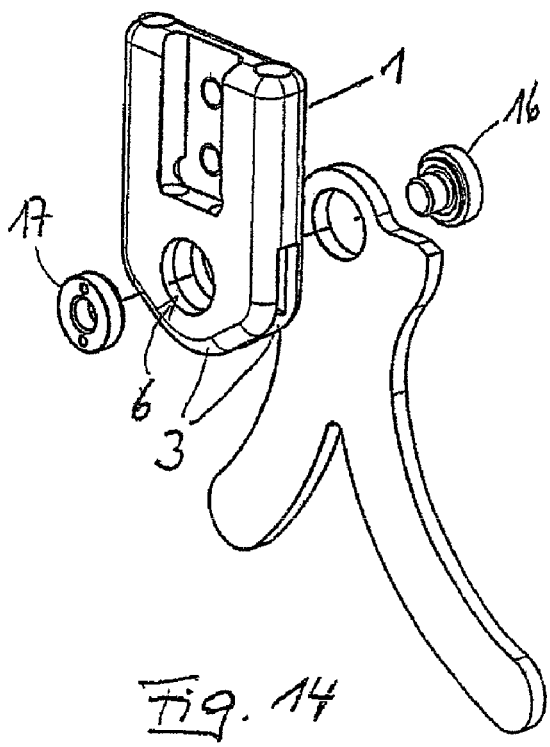
FIG. 14 shows an exploded perspective view of the parts of a fourth embodiment of a rotating joint according to the invention.
Figure 15:
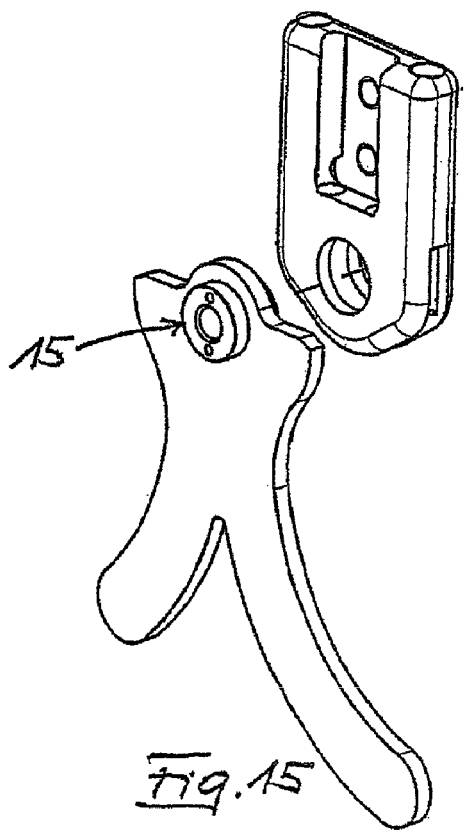
FIG. 15 shows a perspective view illustrating the design of a rotationally fixed unit made up of shaft arrangement and inner joint piece.
Figure 17:
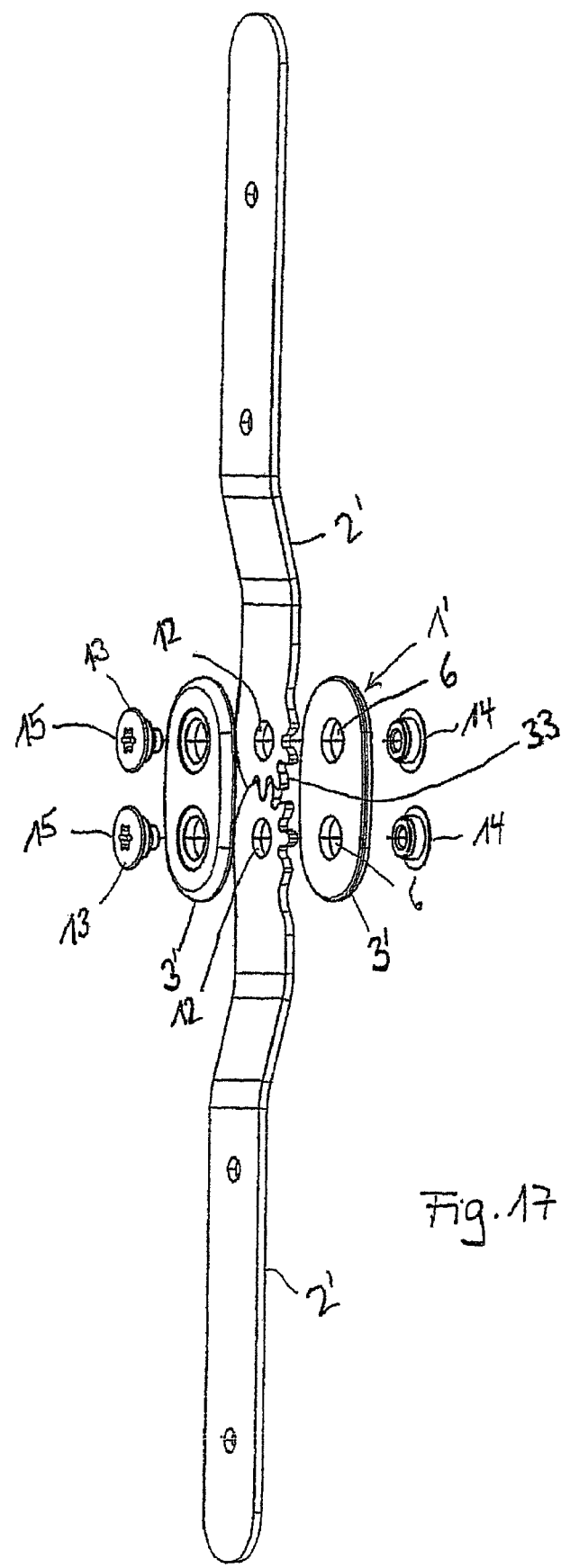
FIG. 17 shows an exploded perspective view of the parts of a fifth embodiment of a rotating joint according to the invention that is made up of two meshing inner joint pieces and of a common outer joint piece.
Figure 18:
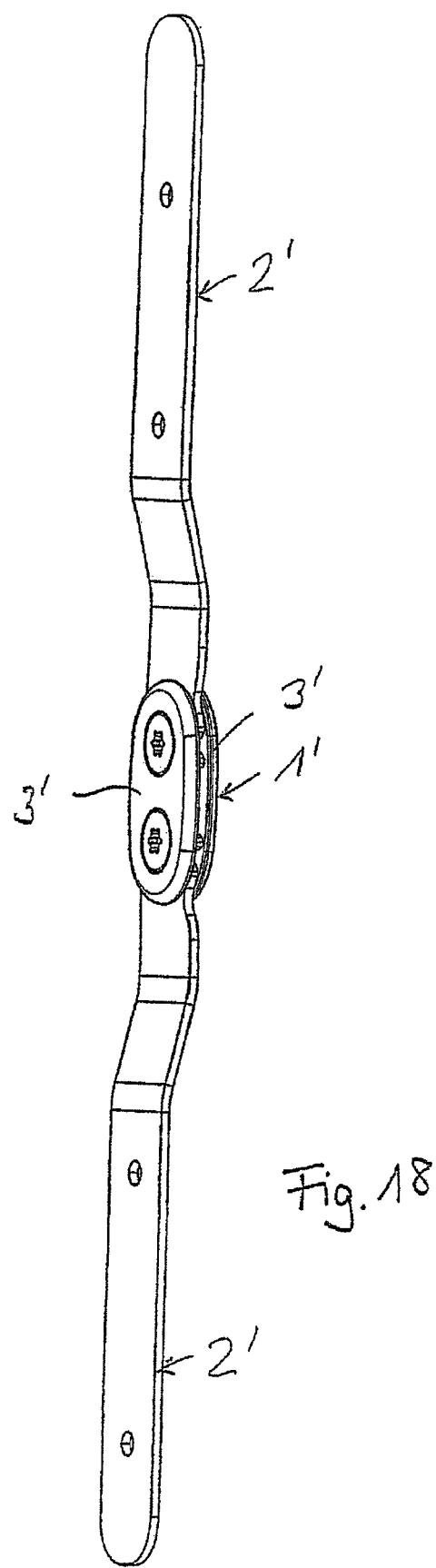
FIG. 18 shows a perspective view of the assembled rotating joint according to the fifth embodiment.

The fourth embodiment of the invention, shown in FIGS. 14 to 16, corresponds to the first embodiment of FIGS. 1 to 7, but without the slide-bearing sleeves 7. The screw head 16 and the threaded pin 17 and the inner wall of the through-holes 6 in the branches 3 of the outer joint piece 1 are designed as slide bearings, which is made possible by a choice of a suitable material or by a surface treatment of the slide-bearing surfaces The fifth embodiment of a rotating joint according to the invention, shown in FIGS. 17 and 18, is composed of two inner joint pieces 2', and of an outer joint piece 1' that is composed of two individual parts forming the branches 3'. The outer joint piece 1' is thus common to both inner joint pieces 2'. Accordingly, the branches 3' of the outer joint piece 1' have two through-holes 6 that are each aligned with a through-hole 12 of one of the inner joint pieces 2'.

Accordingly, the rotating joint is formed by two shaft arrangements 15 which, as in the described fourth embodiment, are composed of a screwed union formed by a screw 13 and screw bushing 14. In this embodiment too, the use of slide-bearing sleeves 7 can be dispensed with by virtue of a suitable choice of material or a suitable design.

Between the shaft arrangements 15, the two inner joint pieces 2' abut one another via respective outer toothed formations 33 that mesh with one another. In this way, the rotation movements of the two inner joint pieces 2' relative to the outer joint piece 1' are synchronized, which is useful for the design of a knee joint, for example for an orthosis. The shape of the inner joint piece 2' is adapted for this purpose.

Without any additional complexity, the rotating joint according to the invention permits increased tilt stability together with a narrow structure of the rotating joint.

The invention claimed is:

1. A tilt-stable rotating joint comprising:
   an outer joint piece including a slit formed by a pair of flat opposing walls and a pair of aligned outer through-holes in both walls;
   an inner joint piece rotatably mounted to the outer joint piece, the inner joint piece including a substantially flat portion positioned between the flat opposing walls and within the slit of the outer joint piece, wherein an inner through-hole extends through the flat portion such that the inner through-hole is aligned with the pair of outer through-holes; and
   a shaft arrangement extending through the outer and inner through-holes, the shaft arrangement including a first section mounted to the inner joint piece at the inner through-hole in a rotationally fixed manner, a portion of the first section protruding from each side of the inner through-hole, the protruding portions of the first section positioned within the outer through-holes, with the shaft arrangement forming bearing surfaces between inner surfaces of the outer through-holes and the protruding portions of the first section.

2. The rotating joint of claim 1, wherein annular edges of the outer through-holes between the inner walls of the opening and surfaces of the inner joint piece form bearing surfaces.

3. The rotating joint of claim 2, wherein the annular edges protrude as raised edges from the remainder of the inner walls.

4. The rotating join of claim 1, wherein the shaft arrangement comprises a pair of bearing sleeves inserted into the outer through-holes.

5. The rotating joint of claim 4, wherein the bearing sleeves each include a circular flange that bears on the inner walls of the opening.

6. The rotating joint of claim 4, wherein the bearing sleeves are pressed into the outer through-holes.

7. A tilt-stable rotating joint comprising:
   an outer joint piece including an opening formed by a pair of inner opposing walls and a pair of aligned outer through-holes in both walls;
   an inner joint piece rotatably mounted to the outer joint piece, the inner joint piece including a substantially flat portion having an inner through-hole, the flat portion positioned within the opening of the outer joint piece such that the inner through-hole is aligned with the pair of outer through-holes; and
   a shaft arrangement extending through the outer and inner through-holes, the shaft arrangement including a first section mounted to the inner joint piece at the inner through-hole in a rotationally fixed manner, a portion of the first section protruding from each side of the inner through-hole, the protruding portions of the first section positioned within the outer through-holes, with the shaft arrangement forming bearing surfaces between inner surfaces of the outer through-holes and the protruding portions of the first section,
   wherein the shaft arrangement comprises a screwed union including a screw and a screw bushing, and wherein the screw and the screw bushing each include an external diameter sized to fit within the internal diameter of the outer through-holes and, when screwed together, the screw and screw bushing of the screwed union, form a radially open groove whose diameter at the groove base is sized to fit within the internal diameter of the inner through-hole of the inner joint piece.

8. The rotating joint of claim 7, wherein the screwed union comprises bearing material around the external diameters.

9. The rotating joint of claim 7, wherein the radially open groove of the screwed union is formed by a shoulder in the external diameter of at least one of the screw and screw bushing.

10. The rotating joint of claim 9, wherein the shoulder is located in both the screw and the screw bushing.

11. A tilt-stable rotating joint comprising:
    an outer joint piece including two joint piece halves that form an opening therebetween, each half including a pair of outer through-holes positioned to be aligned with the other half's through-holes;
    an inner joint piece including two separate flat bar portions that extend away from the outer joint piece and toothed portions that rotatably mate together, each flat bar portion including an inner through-hole positioned such that when the toothed portions are mated together the inner through-holes align with the pairs of outer through-holes; and
    two shaft arrangements each extending through the aligned outer and inner through-holes, each shaft arrangement including a first section mounted to the inner joint piece at the inner through-hole in a rotationally fixed manner, a portion of the first section protruding from each side of the inner through-hole, the protruding portions of the first section positioned within the outer through-holes, with the shaft arrangement forming bearing surfaces between inner surfaces of the outer through-holes and the protruding portions of the first section.

12. A technical orthopedic component comprising at least one tilt-stable rotating joint, the tilt-stable joint including:
    an outer joint piece including a slit formed by a pair of flat opposing walls and a pair of aligned outer through-holes in both walls;
    an inner joint piece rotatably mounted to the outer joint piece, the inner joint piece including a substantially flat portion positioned between the flat opposing walls and within the slit of the outer joint piece, wherein an inner through-hole extends through the flat portion such that the inner through-hole is aligned with the pair of outer through-holes; and
    a shaft arrangement extending through the outer and inner through-holes, the shaft arrangement including a first section mounted to the inner joint piece at the inner through-hole in a rotationally fixed manner, a portion of the first section protruding from each side of the inner through-hole, the protruding portions of the first section positioned within the outer through-holes, with the shaft arrangement forming bearing surfaces between inner surfaces of the outer through-holes and the protruding portions of the first section.

13. The technical orthopedic component of claim 12, further comprising two tilt-stable rotating joints.

14. The technical orthopedic component of claim 13, wherein the two tilt-stable rotating joints are configured in a knee orthosis.

15. A technical orthopedic component comprising at least one tilt-stable rotating joint, the tilt-stable joint including:
    an outer joint piece including an opening formed by a pair of inner opposing walls and a pair of aligned outer through-holes in both walls;
    an inner joint piece rotatably mounted to the outer joint piece, the inner joint piece including a substantially flat portion having an inner through-hole, the flat portion positioned within the opening of the outer joint piece such that the inner through-hole is aligned with the pair of outer through-holes; and a shaft arrangement extending through the outer and inner through-holes, the shaft arrangement including a first section mounted to the inner joint piece at the inner through-hole in a rotationally fixed manner, a portion of the first section protruding from each side of the inner through-hole, the protruding portions of the first section positioned within the outer through-holes, with the shaft arrangement forming bearing surfaces between inner surfaces of the outer through-holes and the protruding portions of the first section, wherein the shaft arrangement comprises a screwed union including a screw and a screw bushing, and wherein the screw and the screw bushing each include an external diameter sized to fit within the internal diameter of the outer through-holes and, when screwed together, the screw and screw bushing of the screwed union, form a radially open groove whose diameter at the groove base is sized to fit within the internal diameter of the inner through-hole of the inner joint piece.

16. The technical orthopedic component of claim 15 comprising two tilt-stable rotating joints wherein the two shaft arrangements each comprise a screwed union including a screw and a screw bushing.

17. A technical orthopedic component comprising at least one tilt-stable rotating joint, the tilt-stable joint including:

an outer joint piece including two joint piece halves that form an opening therebetween, each half including a pair of outer through-holes positioned to be aligned with the other half's through-holes;

an inner joint piece including two separate flat bar portions that extend away from the outer joint piece and toothed portions that rotatably mate together, each flat bar portion including an inner through-hole positioned such that when the toothed portions are mated together the inner through-holes align with the pairs of outer through-holes; and two shaft arrangements each extending through the aligned outer and inner through-holes, each shaft arrangement including a first section mounted to the inner joint piece at the inner through-hole in a rotationally fixed manner, a portion of the first section protruding from each side of the inner through-hole, the protruding portions of the first section positioned within the outer through-holes, with the shaft arrangement forming bearing surfaces between inner surfaces of the outer through-holes and the protruding portions of the first section.

18. A tilt-stable rotating joint comprising:

an outer joint piece including an opening formed by a pair of inner opposing walls and a pair of aligned outer through-holes in both walls;

an inner joint piece rotatably mounted to the outer joint piece, the inner joint piece including a substantially flat portion having an inner through-hole, the flat portion positioned within the opening of the outer joint piece such that the inner through-hole is aligned with the pair of outer through-holes; and a shaft arrangement extending through the outer and inner through-holes, the shaft arrangement including a first section mounted to the inner joint piece at the inner through-hole in a rotationally fixed manner, a portion of the first section protruding from each side of the inner through-hole, the protruding portions of the first section positioned within the outer through-holes, with the shaft arrangement forming bearing surfaces between inner surfaces of the outer through-holes and the protruding portions of the first section, wherein the shaft arrangement comprises a pair of bushings connected by a rivet and wherein the bushings each include an external diameter sized to fit within the internal diameter of the outer through-holes and, when screwed together, the screw and screw bushing of the screwed union, form a radially open groove whose diameter at the groove base is sized to fit within the internal diameter of the inner through-hole of the inner joint piece.

19. A technical orthopedic component comprising at least one tilt-stable rotating joint, the tilt-stable joint including:

an outer joint piece including an opening formed by a pair of inner opposing walls and a pair of aligned outer through-holes in both walls;

an inner joint piece rotatably mounted to the outer joint piece, the inner joint piece including a substantially flat portion having an inner through-hole, the flat portion positioned within the opening of the outer joint piece such that the inner through-hole is aligned with the pair of outer through-holes; and a shaft arrangement extending through the outer and inner through-holes, the shaft arrangement including a first section mounted to the inner joint piece at the inner through-hole in a rotationally fixed manner, a portion of the first section protruding from each side of the inner through-hole, the protruding portions of the first section positioned within the outer through-holes, with the shaft arrangement forming bearing surfaces between inner surfaces of the outer through-holes and the protruding portions of the first section, wherein the shaft arrangement comprises a pair of bushings connected by a rivet and wherein the bushings each include an external diameter sized to fit within the internal diameter of the outer through-holes and, when screwed together, the screw and screw bushing of the screwed union, form a radially open groove whose diameter at the groove base is sized to fit within the internal diameter of the inner through-hole of the inner joint piece.

* * * * *